United States Patent

Jensen-Korte et al.

[11] Patent Number: 4,971,989
[45] Date of Patent: Nov. 20, 1990

[54] SUBSTITUTED 1-ARYLPYRAZOLES, PESTICIDAL COMPOSITIONS AND USE

[75] Inventors: Uta Jensen-Korte, Duesseldorf; Schallner, Otto, Monheim, both of Fed. Rep. of Germany; Benedikt Becker, Bolzano, Italy; Jürgen Hartwig, Leverkusen; Wilhelm Stendel, Wuppertal, both of Fed. Rep. of Germany

[73] Assignee: Bayer Aktiengesellschaft, Leverkusen, Fed. Rep. of Germany

[21] Appl. No.: 497,470

[22] Filed: Mar. 22, 1990

[30] Foreign Application Priority Data

Apr. 8, 1989 [DE] Fed. Rep. of Germany ....... 3911556

[51] Int. Cl.$^5$ ............. A61K 43/40; A61K 43/56; C07D 231/44; C07D 401/04
[52] U.S. Cl. ................... 514/404; 514/158; 514/184; 514/189; 514/341; 514/407; 546/5; 546/279; 548/104; 548/362; 548/376; 424/45
[58] Field of Search ........... 546/5, 279; 548/104, 548/362, 376; 514/158, 184, 189, 341, 404, 407; 424/45

[56] References Cited

U.S. PATENT DOCUMENTS

4,804,675  2/1989  Jensen-Korte et al. ............ 514/407
4,863,937  9/1989  Gehring et al. .................... 548/376

Primary Examiner—Robert W. Ramsuer
Attorney, Agent, or Firm—Sprung, Horn, Kramer & Woods

[57] ABSTRACT

Substituted 1-arylpyrazoles useful in combating insects having the arachnida and nematodes of the formula

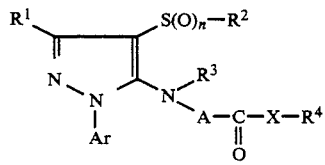

in which
$R^1$ represents hydrogen or alkyl,
$R^2$ represents alkyl or halogenoalkyl,
$R^3$ represents hydrogen or alkanoyl,
$R^4$ represents hydrogen, alkyl, hydroxyalkyl, alkoxyalkyl, alkylthioalkyl, halogenoalkyl, alkenyl, halogenoalkenyl or alkinyl, in each case optionally substituted cycloalkyl, aralkyl or aryl, or, when X represents oxygen or sulphur, $R^4$ can represent a cation equivalent which is bonded in a salt-like manner,
A represents a double-linked alkylene radical,
X represents oxygen, sulphur or a radical

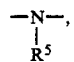

Ar represents optionally substituted phenyl, pyridyl and
n represents a number 0, 1 or 2, where $R^5$ represents hydrogen, alkyl, hydroxylalkyl, alkoxyalkyl, alylthioalkyl, halogenoalkyl, alkenyl, halogenoalkenyl or alkinyl, or represents optionally substituted cycloalkyl, aralkyl or aryl.

6 Claims, No Drawings

SUBSTITUTED 1-ARYLPYRAZOLES, PESTICIDAL COMPOSITIONS AND USE

The invention relates to new substituted 1-arylpyrazoles, to several processes for their preparation, and to their use as pesticides.

It is known that certain substituted 1-arylpyrazoles, such as, for example, the compound 5-amino-1-(2,6-dichloro-4-trifluoromethylphenyl)-4-methylthiopyrazole or the compound 5-amino-1-(2,6-dichloro-4-trifluoromethylphenyl)-3-methyl-4-dichlorofluoromethylthiopyrazole or the compound 1-(2,6-dichloro-4-trifluoromethylphenyl)-3-methyl-4-dichlorofluoromethylsulphonyl-5-propionamidopyrazole or the compound 5-amino-1-(2,6-dichloro-4-trifluoromethylphenyl)-3-methyl-4-dichloro-fluoromethylsulphinyl-pyrazole or the compound 5-amino-1-(2,6-dichloro-4-trifluoromethylphenyl)-4-trifluoromethylsulphinyl-pyrazole, have a good activity against pests (cf., for example, EP-A 201,852).

However, the level of activity or duration of activity of these previously known compounds is not entirely satisfactory in all fields of application, in particular in the case of certain insects or when low application concentrations are used.

New substituted 1-arylpyrazoles of the general formula (I)

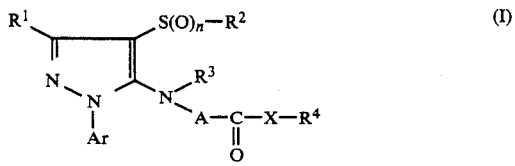

in which
R$^1$ represents hydrogen or alkyl,
R$^2$ represents alkyl or halogenoalkyl,
R$^3$ represents hydrogen or alkanoyl,
R$^4$ represents hydrogen, alkyl, hydroxyalkyl, alkoxyalkyl, alkylthioalkyl, halogenoalkyl, alkenyl, halogenoalkenyl or alkinyl, or represents in each case optionally substituted cycloalkyl, aralkyl or aryl, or, in the event that X represents oxygen or sulphur, also represents a cation equivalent which is bonded in a salt-like manner,
A represents a double-linked alkylene radical,
X represents oxygen, sulphur or a radical

Ar represents optionally substituted phenyl or optionally substituted pyridyl and
n represents a number 0, 1 or 2, where R$^5$ represents hydrogen, alkyl, hydroxyalkyl, alkoxyalkyl, alkylthioalkyl, halogenoalkyl, alkenyl, halogenoalkenyl or alkinyl, or represents optionally substituted cycloalkyl, aralkyl or aryl,
have now been found.

Furthermore, it has been found that the new substituted 1-arylpyrazoles of the general formula (I)

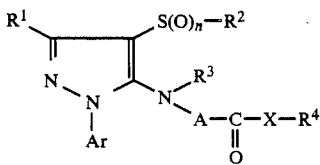

in which
R$^1$ represents hydrogen or alkyl,
R$^2$ represents alkyl or halogenoalkyl,
R$^3$ represents hydrogen or alkanoyl,
R$^4$ represents hydrogen, alkyl, hydroxyalkyl, alkoxyalkyl, alkylthioalkyl, halogenoalkyl, alkenyl, halogenoalkenyl or alkinyl, or represents in each case optionally substituted cycloalkyl, aralkyl or aryl, or, in the event that X represents oxygen or sulphur, also represents a cation equivalent which is bonded in a salt-like manner,
A represents a double-linked alkylene radical,
X represents oxygen, sulphur or a radical

Ar represents optionally substituted phenyl or optionally substituted pyridyl and
n represents a number 0, 1 or 2, where R$^5$ represents hydrogen, alkyl, hydroxyalkyl, alkoxyalkyl, alkylthioalkyl, halogenoalkyl, alkenyl, halogenoalkenyl or alkinyl, or represents optionally substituted cycloalkyl, aralkyl or aryl,
are obtained by one of the processes described below:
(a) substituted 1-arylpyrazoles of the formula (I)

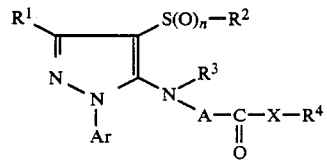

in which
R$^1$, R$^2$, R$^3$, R$^4$, A, X, Ar and n have the abovementioned meaning,
are obtained when 1-arylpyrazoles of the formula (II)

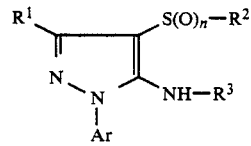

in which
R$^1$, R$^2$, R$^3$, Ar and n have the abovementioned meaning, are reacted with alkylating agents of the formula (III)

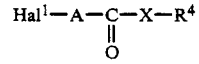

in which
Hal$^1$ represents halogen and

R⁴, A and X have the abovementioned meaning, if appropriate in the presence of a diluent and if appropriate in the presence of a reaction auxiliary;

(b) substituted 1-arylpyrazoles of the formula (Ib)

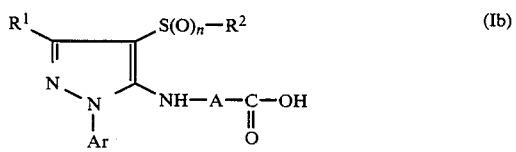

in which
R¹, R², A, Ar and n have the abovementioned meaning, are obtained when substituted 1-arylpyrazoles of the formula (Ia)

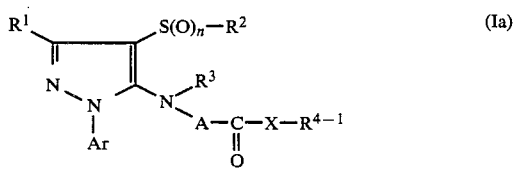

in which
R⁴⁻¹ represents alkyl, hydroxyalkyl, alkoxyalkyl, alkylthioalkyl, halogenoalkyl, alkenyl, halogenoalkenyl or alkinyl, or represents in each case optionally substituted cycloalkyl, aralkyl or aryl and
R¹, R², R³, A, X, Ar and n have the abovementioned meaning,
are hydrolyzed with acids or bases as a catalyst in the presence of water and, if appropriate, in the presence of a diluent;

(c) substituted 1-arylpyrazoles of the formula (Ic)

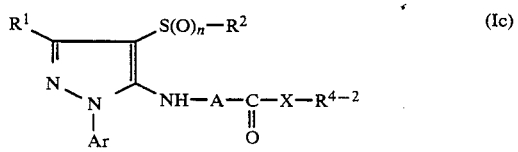

in which
R⁴⁻² represents hydrogen, alkyl, hydroxyalkyl, alkoxyalkyl, alkylthioalkyl, halogenoalkyl, alkenyl, halogenoalkenyl or alkinyl, or represents in each case optionally substituted cycloalkyl, aralkyl or aryl and
R¹, R², A, X, Ar and n have the abovementioned meaning,
are obtained when substituted 1-arylpyrazoles of the formula (Ib)

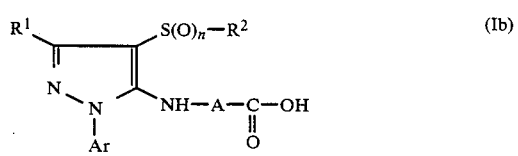

in which
R¹, R², A and n have the abovementioned meaning, are reacted with alcohols, thiols or amino compounds of the formula (IV)

R⁴⁻²—X—H            (IV)

in which
R⁴⁻² and X have the abovementioned meaning, in the presence of an acylation catalyst and, if appropriate, in the presence of a diluent and, if appropriate, in the presence of a reaction auxiliary;

(d) substituted 1-arylpyrazoles of the formula (Id)

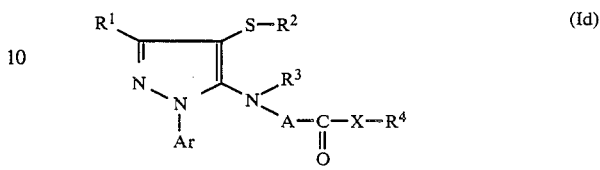

in which
R¹, R², R³, R⁴, A, X and Ar have the abovementioned meaning,
are obtained when 1-arylpyrazoles which are unsubstituted in the 4-position, of the formula (V),

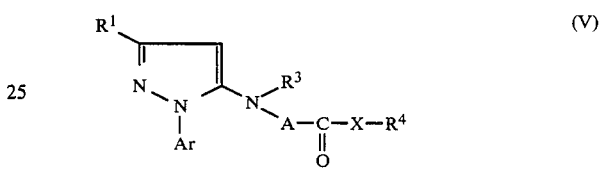

in which
R¹, R³, R⁴, A, X and Ar have the abovementioned meaning,
are reacted with sulphenyl halides of the formula (VI)

R²—S—Hal²            (VI)

in which
Hal² represents halogen and
R² has the abovementioned meaning, if appropriate in the presence of a diluent and, if appropriate, in the presence of a reaction auxiliary;

(e) substituted 1-arylpyrazoles of the formula (Ie)

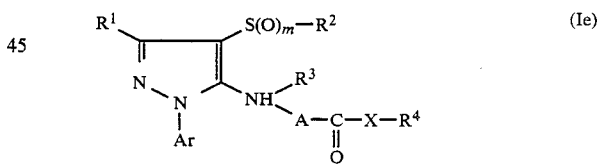

in which
R¹, R², R³, R⁴, A, X and Ar have the abovementioned meaning and
m represents a number 1 or 2,
are obtained when substituted 1-arylpyrazoles of the formula (Id)

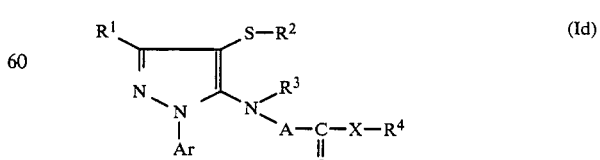

in which
R¹, R², R³, R⁴, A, X and Ar have the abovementioned meaning, are reacted with oxidants, if appropriate in the presence of a diluent and, if appropriate, in the presence of a catalyst;

(f) substituted 1-arylpyrazoles of the formula (If)

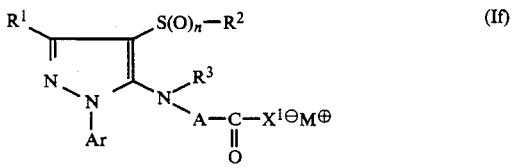

in which
X¹ represents oxygen or sulphur,
M⊕ represents a cation which is bonded in a saltlike manner and
R¹, R², R³, A, Ar and n have the abovementioned meaning,
are obtained when substituted 1-arylpyrazoles of the formula (Ig)

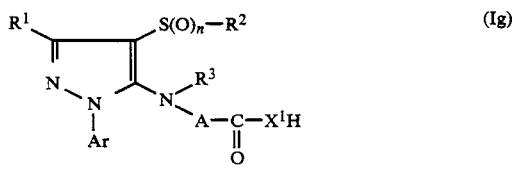

in which
R¹, R², R³, A, X¹, Ar and n have the abovementioned meaning,
are reacted with inorganic or organic bases, if appropriate in the presence of a diluent.

Finally, it has been found that the new substituted 1-arylpyrazoles of the general formula (I) have a good activity against pests, in particular against leaf insects and soil insects which damage plants.

Surprisingly, the substituted 1-arylpyrazoles of the general formula (I) according to the invention have a considerably better activity against pests than the substituted 1-arylpyrazoles which are known from the prior art, such as, for example, the compound 5-amino-1-(2,6-dichloro-4-trifluoromethylphenyl)-4-methylthiopyrazole or the compound 5-amino-1-(2,6-dichloro-4-trifluoromethylphenyl)-3-methyl-4-dichlorofluoromethylthiopyrazole or the compound 1-(2,6-dichloro-4-trifluoromethylphenyl)-3-methyl-4-dichlorofluoromethylsulphonyl-5-propionamidopyrazole or the compound 5-amino-1-(2,6-dichloro-4-trifluoromethylphenyl)-3-methyl-4-dichlorofluoromethylsulphinyl-pyrazole or the compound 5-amino-1-(2,6-dichloro-4-trifluoromethylphenyl)-4-trifluoromethylsulphinyl-pyrazole, which are compounds of a similar chemical structure and similar type of action.

Formula (I) provides a general definition of the substituted 1-arylpyrazoles according to the invention. Preferred compounds of the formula (I) are those in which R¹ represents hydrogen or straight-chain or branched alkyl having 1 to 6 carbon atoms, R² represents straight-chain or branched alkyl having 1 to 6 carbon atoms or straight-chain or branched halogenoalkyl having 1 to 4 carbon atoms and 1 to 9 identical or different halogen atoms, R³ represents hydrogen or straight-chain or branched alkanoyl having 1 to 5 carbon atoms, R⁴ represents hydrogen, in each case straight-chain or branched alkyl or hydroxyalkyl, each of which has 1 to 12 carbon atoms, in each case straight-chain or branched alkoxyalkyl or alkylthioalkyl, each of which has 2 to 12 carbon atoms, in each case straight-chain or branched alkenyl or alkinyl, each of which has 2 to 12 carbon atoms, straight-chain or branched halogenoalkyl having 1 to 8 carbon atoms and 1 to 17 identical or different halogen atoms, straight-chain or branched halogenoalkenyl having 2 to 8 carbon atoms and 1 to 15 identical or different halogen atoms, cycloalkyl which has 3 to 7 carbon atoms and which is optionally monosubstituted or polysubstituted by identical or different alkyl substituents which have 1 to 4 carbon atoms and which are straight-chain or branched, or represents phenyl, benzyl or phenylethyl, each of which is optionally monosubstituted or polysubstituted in the phenyl moiety by identical or different substituents, suitable phenyl substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and also phenyl which is optionally monosubstituted or polysubstituted by identical or different substituents from the series comprising halogen and/or straight-chain or branched alkyl having 1 to 4 carbon atoms; and, furthermore, in the event that X represents oxygen or sulphur, also represents one equivalent of an alkali metal, alkaline earth metal, copper, zinc, manganese, tin, iron-cobalt or nickel cation or an ammonium, phosphonium or sulphonium cation, each of which is optionally monosubstituted or polysubstituted by identical or different substituents, suitable substituents being: straight-chain or branched alkyl having 1 to 18 carbon atoms, phenyl or benzyl, A represents a double-linked, straight-chain or branched alkylene radical having 1 to 12 carbon atoms, X represents oxygen, sulphur or a radical

Ar represents phenyl, 2-pyridyl, 3-pyridyl or 4-pyridyl, each of which is optionally monosubstituted or polysubstituted by identical or different substituents, suitable substituents in each case being: cyano, nitro, halogen, in each case straight-chain or branched alkyl, alkoxy or alkoxycarbonyl, each of which has 1 to 4 carbon atoms, in each case straight-chain or branched halogenoalkyl or halogenoalkoxy, each of which has 1 to 4 carbon atoms and 1 to 9 identical or different halogen atoms, or a radical —S(O)$_p$—R⁶ and n represents a number 0, 1 or 2, where R⁵ represents hydrogen, in each case straight-chain or branched alkyl or hydroxyalkyl, each of which has 1 to 12 carbon atoms, in each case straight-chain or branched alkoxyalkyl or alkylthioalkyl, each of which has 2 to 12 carbon atoms, in each case straight-chain or branched alkenyl or alkinyl, each of which has 2 to 12 carbon atoms, in each case straight-chain or branched halogenoalkyl having 1 to 8 carbon atoms and 1 to 17 identical or different halogen atoms, straight-chain or branched halogenoalkenyl having 2 to 8 carbon atoms and 1 to 15 identical or different halogen atoms, or cycloalkyl which has 3 to 7 carbon atoms and which is optionally monosubstituted or polysubstituted by identical or different alkyl substituents which are straight-chain or branched and which have 1 to 4 carbon atoms, or represents phenyl, benzyl or phenylethyl, each of which is optionally monosubstituted or polysubstituted in the phenyl moiety by identical or different substituents, suitable phenyl substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and also phenyl which is optionally monosubstituted or polysubstituted by identical or different substituents from the series comprising halogen and/or straight-chain or branched alkyl having 1 to 4 carbon atoms;

$R^6$ represents amino and in each case optionally straight-chain or branched alkyl, alkylamino, dialkylamino or halogenoalkyl, in each case having to 4 carbon atoms in the individual alkyl moieties and, in the case of the halogenoalkyl, 1 to 9 identical or different halogen atoms, and p represents a number 0, 1 or 2.

Particularly preferred compounds of the formula (I) are those in which $R^1$ represents hydrogen, methyl, ethyl, n- or i-propyl, n-, i-, s- or t-butyl, $R^2$ represents methyl, ethyl, n- or i-propyl, n-, i-, s- or t-butyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl or bromopropyl, $R^3$ represents hydrogen, acetyl, propionyl or butyryl, $R^4$ represents hydrogen, or methyl, ethyl, n- or i-propyl, n-, i-, s- or t-butyl or n- or i-pentyl, each of which is optionally monosubstituted to trisubstituted by identical or different substituents from the series comprising fluorine, chlorine, hydroxyl, methoxy, ethoxy, methylthio or ethylthio, or allyl, propenyl or butenyl, each of which is optionally monosubstituted to trisubstituted by identical or different substituents from the series comprising fluorine and chlorine, or propargyl, propinyl, butinyl or pentinyl, or cyclopropyl, cyclopentyl or cyclohexyl, or benzyl or phenyl, each of which is optionally monosubstituted to pentasubstituted by identical or different substituents from the series comprising fluorine, chlorine, bromine, cyano, nitro, methyl, ethyl, methoxy, ethoxy, methylthio or trifluoromethyl, and, in the event that X represents oxygen or sulphur, furthermore also represents one equivalent of a sodium, potassium, magnesium, calcium, barium, copper, zinc, manganese, tin, iron, cobalt or nickel cation, or an ammonium, phosphonium or sulphonium cation, each of which is optionally monosubstituted to tetrasubstituted by identical or different substituents from the series comprising methyl, ethyl, n- or i-propyl, n-, i-, s- or t-butyl, benzyl or phenyl, A represents a double-linked, straight-chain or branched alkylene radical having 1 to 6 carbon atoms, X represents oxygen, sulphur or a radical

Ar represents phenyl which is optionally monosubstituted to pentasubstituted by identical or different substituents, or 2-pyridyl which is optionally monosubstituted to tetrasubstituted by identical or different substituents, suitable substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $—S(O)_p—R^6$ and n represents a number 0, 1 or 2, where $R^5$ represents hydrogen, or methyl, ethyl, n- or i-propyl, n-, i-, s- or t-butyl or n- or i-pentyl, each of which is optionally monosubstituted to trisubstituted by identical or different substituents from the series comprising fluorine, chlorine, hydroxyl, methoxy, ethoxy, methylthio or ethylthio, or allyl, propenyl or butenyl, each of which is optionally monosubstituted to trisubstituted by identical or different substituents from the series comprising fluorine and chlorine, or propargyl, propinyl, butinyl or pentinyl, or cyclopropyl, cyclopentyl or cyclohexyl, or represents benzyl or phenyl, each of which is optionally monosubstituted to pentasubstituted by identical or different substituents from the series comprising fluorine, chlorine, bromine, cyano, nitro, methyl, ethyl, methoxy, ethoxy, methylthio or trifluoromethyl, $R^6$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, and p represents a number 0, 1 or 2.

Very particularly preferred compounds of the formula (I) are those in which $R^1$ represents hydrogen or methyl, $R^2$ represents methyl, ethyl, n- or i-propyl, trifluoromethyl, dichlorofluoromethyl or chlorodifluoromethyl, $R^3$ represents hydrogen, acetyl or propionyl, $R^4$ represents methyl, ethyl, n- or i-propyl, n-, i-, s- or t-butyl, n- or i-pentyl, allyl, propenyl, n- or i-butenyl, n- or i-pentenyl, propargyl, propinyl, n- or i-butinyl, n- or i-pentinyl, trifluoroethyl, trichloroethyl, chloroethyl, chloropropenyl, dichloropropenyl, hydroxyethyl, hydroxypropyl, methoxymethyl, methoxyethyl, methoxypropyl, ethoxymethyl, ethoxyethyl, ethoxypropyl, propoxymethyl, propoxyethyl, butoxymethyl, butoxyethyl, methylthiomethyl, methylthioethyl, methylthiopropyl, ethylthioethyl, ethylthiopropyl or propylthioethyl, and, in the event that X represents oxygen or sulphur, furthermore also represents a sodium or potassium ion or represents an ammonium ion which is optionally monosubstituted to tetrasubstituted by identical or different substituents from the series comprising methyl, ethyl, n- or i-propyl, n-butyl or benzyl, A represents a double-linked, straight-chain or branched alkylene radical having 1 to 4 carbon atoms, X represents oxygen, sulphur or

Ar represents phenyl which is optionally monosubstituted to pentasubstituted by identical or different substituents, suitable substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl and n represents a number 0, 1 or 2, where $R^5$ represents hydrogen, methyl, ethyl, n- or i-propyl, n-, i-, s- or t-butyl, n- or i-pentyl, allyl, propenyl, n- or i-butenyl, n- or i-pentenyl, propargyl, propinyl, n- or i-butinyl, n- or i-pentinyl, trifluoroethyl, trichloroethyl, chloroethyl, chloropropenyl, dichloropropenyl, hydroxyethyl, hydroxypropyl, methoxymethyl, methoxyethyl, methoxypropyl, ethoxymethyl, ethoxyethyl, ethoxypropyl, methylthiomethyl, methylthioethyl, methylthiopropyl, ethylthioethyl or ethylthiopropyl.

Besides, other compounds of the formula (I) which are very particularly preferred are those in which $R^1$ represents hydrogen or methyl, $R^2$ represents methyl, ethyl, n- or i-propyl, trifluoromethyl, dichlorofluoromethyl or chlorodifluoromethyl, $R^3$ represents hydrogen, $R^4$ represents hydrogen or one equivalent of a sodium, potassium, calcium, magnesium, barium, copper, zinc, manganese, tin, iron, cobalt or nickel cation, or an ammonium cation which is optionally monosubstituted to tetrasubstituted by identical or different substituents from the series comprising methyl, ethyl, n- or i-propyl, n-, i- or s-butyl, benzyl or phenyl, A represents a double-linked, straight-chain or branched alkylene radical having 1 to 4 carbon atoms, X represents oxygen, Ar represents phenyl which is optionally monosubstituted to pentasubstituted by identical or different substituents, suitable substituents being: fluorine, chlorine, bromine, methyl, ethyl, methoxy, ethoxy, trifluoromethyl, trifluoromethylsulphinyl or trifluoromethylsulphonyl and n represents a number 0, 1 or 2.

Especially preferred compounds of the formula (I) are those in which $R^1$ represents hydrogen or methyl, $R^2$ represents trifluoromethyl, dichlorofluoromethyl or chlorodifluoromethyl, $R^3$ represents hydrogen, acetyl or propionyl, $R^4$ represents hydrogen, methyl, ethyl, n- or i-propyl, n-, i-, s- or t-butyl or benzyl, A represents a radical of the formula —CH$_2$—; —CH$_2$—CH$_2$—; —CH$_2$—CH$_2$—CH$_2$— or

X represents oxygen or a radical

Ar represents phenyl which is optionally monosubstituted to pentasubstituted by identical or different substituents from the series comprising fluorine, chlorine, bromine, trifluoromethyl or trifluoromethoxy and n represents a number 0, 1 or 2, where $R^5$ represents methyl, ethyl, n- or i-propyl, n-, i-, s- or t-butyl or a radical —SO$_2$—R$^6$ and $R^6$ represents methyl, trifluoromethyl, phenyl or p-tolyl.

If, for example, 5-acetamido-3-methyl-1-(2,6-dichloro-4-trifluoromethylphenyl)-4-trifluoromethyl-thiopyrazole and methyl bromoacetate are used as the starting substances, the course of the reaction of process (a) according to the invention may be represented by the following equation:

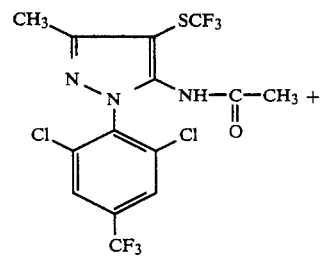

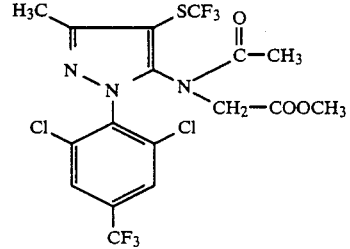

If, for example, 5-[N-methoxycarbonylmethyl)acetamido]-3-methyl-1-(2,6-dichloro-4-trifluoromethylphenyl)-4-trifluoromethylthio-pyrazole is used as the starting compound, the course of the reaction of process (b) according to the invention may be represented by the following equation:

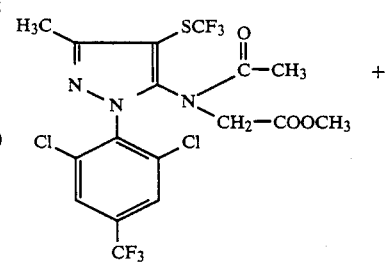

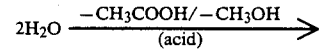

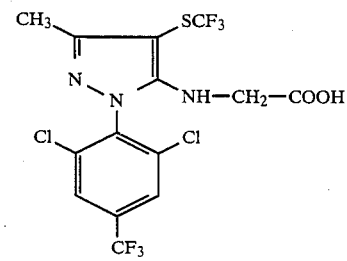

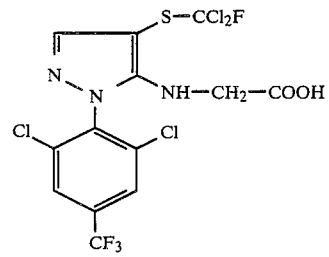

If, for example, N-[4-methylthio-1-(2,4,6-trichlorophenyl)-5-pyrazolyl]-glycine and 2-methoxyethanol are used as the starting substances, the course of the reaction of process (c) according to the invention may be represented by the following equation:

If, for example, 3-methyl-4-methyl-thio)-1-(2,4-dichlorophenyl)-5-ethoxycarbonyl-methylaminopyrazole is used as the starting compound and 3-chloroperbenzoic acid as the oxidant, the course of the reaction of process (e) according to the invention may be represented by the following equation:

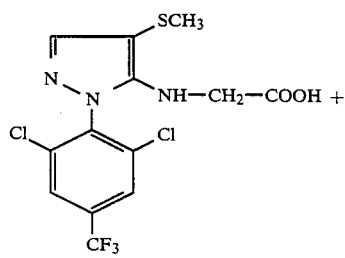

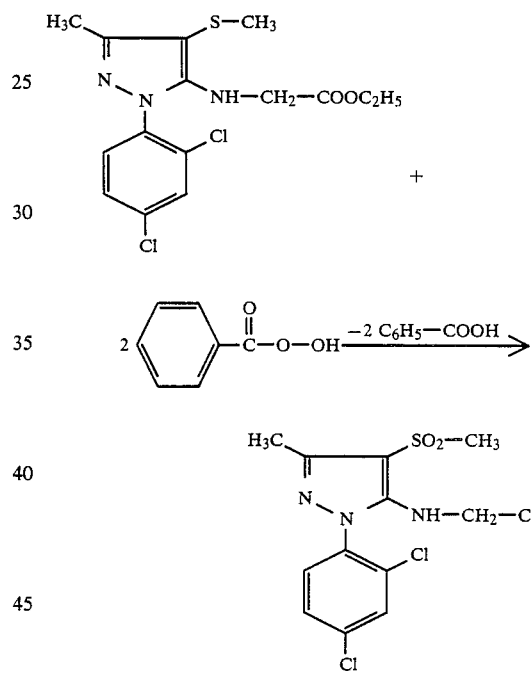

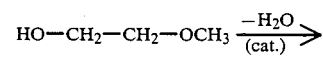

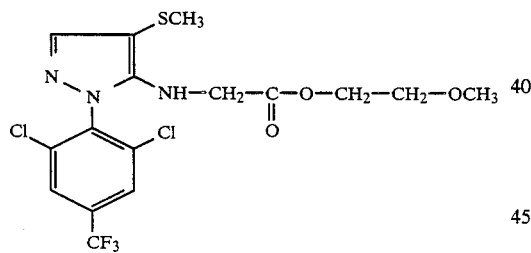

If, for example, N-[1-(2,6-dichloro-4-trifluoromethylphenyl)-5-pyrazolyl]-glycine and dichlorofluoromethanesulphenyl chloride are used as the starting substances, the course of the reaction of process (d) according to the invention may be represented by the following equation:

If, for example, N-[1-(2,6-dichloro-4-trifluoromethylsulphonyl-phenyl)-3-methyl-4-trifluoromethylsulphonyl-5-pyrazolyl]-glycine and triethylamine are used as the starting substances, the course of the reaction of process (f) according to the invention may be represented by the following equation:

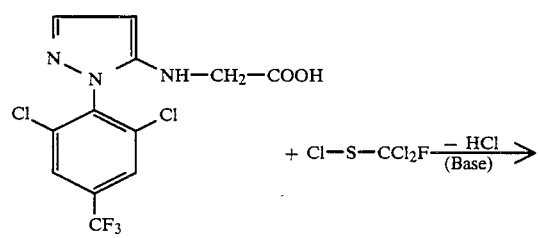

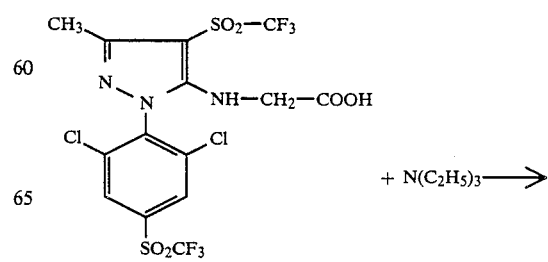

-continued

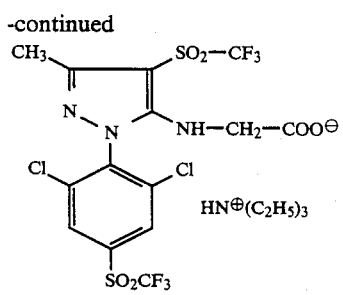

Formula (II) provides a general definition of the 1-arylpyrazoles required as starting substances for carrying out process (a) according to the invention. In this formula (II), $R^1$, $R^2$, $R^3$, Ar and n preferably represent those radicals and indices which have already been mentioned in connection with the description of the substances of the formula (I) according to the invention as being preferred for these substituents and indices.

The 1-arylpyrazoles of the formula (II) are known (cf., for example, EP-A 201,852).

Formula (III) provides a general definition of the alkylating agents furthermore required as starting substances for carrying out process (a) according to the invention. In this formula (III), $R^4$, A and X preferably represent those radicals which have already been mentioned in connection with the description of the substances of the formula (I) according to the invention as being preferred for these substituents.

$Hal^1$ preferably represents chlorine, bromine or iodine, in particular bromine.

The alkylating agents of the formula (III) are generally known compounds of organic chemistry, or they can be obtained in analogy to generally known processes.

Formula (Ia) provides a general definition of the substituted 1-arylpyrazoles required as starting substances for carrying out process (b) according to the invention. In this formula (Ia), $R^1$, $R^2$, $R^3$, A, X, Ar and n preferably represent those radicals which have already been mentioned in connection with the description of the substances of the formula (I) according to the invention as being preferred for this substituent.

$R^{4-1}$ preferably represents those radicals which have already been mentioned in connection with the description of the substances of the formula (I) according to the invention as being preferred for the substituent $R^4$, with the exception of the hydrogen radical and the cations which are bonded in a salt-like manner.

The substituted 1-arylpyrazoles of the formula (Ia) are compounds according to the invention and can be obtained with the aid of processes (a), (c), (d) or (e) according to the invention.

Formula (Ib) provides a general definition of the substituted 1-arylpyrazoles required as starting substances for carrying out process (c) according to the invention. In this formula (Ib), $R^1$, $R^2$, A, Ar and n preferably represent those radicals which have already been mentioned in connection with the description of the substances of the formula (I) according to the invention as being preferred for these substituents.

The substituted 1-arylpyrazoles of the formula (Ib) are compounds according to the invention and can be obtained with the aid of processes (a), (b), (d) or (e) according to the invention.

Formula (IV) provides a general definition of the alcohols, thiols or amino compounds furthermore required as starting substances for carrying out process (c) according to the invention. In this formula (IV), X preferably represents those radicals which have already been mentioned in connection with the description of the substances of the formula (I) according to the invention as being preferred for these substituents.

$R^{4-2}$ preferably represents those radical which have already been mentioned in connection with the description of the substances of the formula (I) according to the invention as being preferred for the substituent $R^4$, with the exception of the cations which are bonded in a salt-like manner.

The alcohols, thiols or amino compounds of the formula (IV) are generally known compounds of organic chemistry.

Formula (V) provides a general definition of the 1-arylpyrazoles which are unsubstituted in the 4-position and which are required as starting substances for carrying out process (d) according to the invention. In this formula (V), $R^1$, $R^3$, $R^4$, A, X and Ar preferably represent those radicals which have already been mentioned in connection with the description of the substances of the formula (I) according to the invention as being preferred for these substituents.

The 1-arylpyrazoles which are unsubstituted in the 4-position, of the formula (V), were hitherto unknown. However, they are obtained in analogy to known processes, for example when 1-arylpyrazoles of the formula (VII)

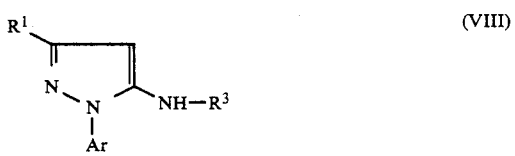

in which $R^1$, $R^3$ and Ar have the abovementioned meaning, are reacted, in analogy to the procedure of process (a) according to the invention, with alkylating agents of the formula (III)

in which

A, X and $R^4$ have the abovementioned meaning and $Hal^1$ represents halogen, in particular bromine, if appropriate in the presence of a diluent, such as, for example, acetonitrile or tetrahydrofuran, and, if appropriate, in the presence of a reaction auxiliary such as, for example, potassium carbonate or sodium hydride, at temperatures between −30° C. and +120° C., or, alternatively, when 1-arylpyrazoles of the formula (VIII)

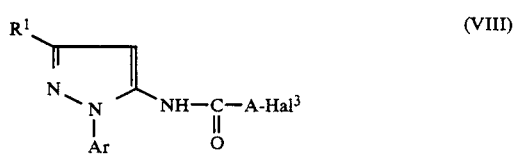

in which $R^1$, A and Ar have the abovementioned meaning and $Hal^3$ represents halogen, in particular chlorine or bromine, in a first step, initially subjected to an intramolecular cyclization reaction with a base, such as, for example, ammonia, if appropriate in the presence of a diluent, such as, for example, ethanol, and then, in a second step, the resulting N-pyrazolyl lactams of the formula (IX)

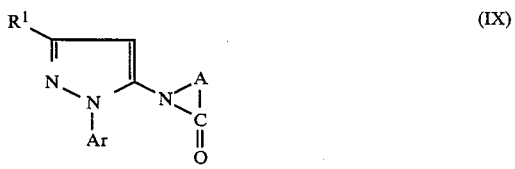

in which

R¹, A and Ar have the abovementioned meaning, are then cleaved again with aqueous acids, such as, for example, hydrobromic acid, at temperatures between 20° C. and 150° C., to give the 1-arylpyrazoles which are unsubstituted in the 4-position, of the formula (Va),

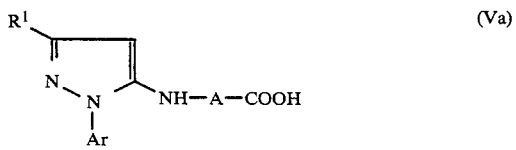

in which

R¹, A and Ar have the abovementioned meaning (cf. also the Preparation Examples).

1-Arylpyrazoles of the formulae (VII) and (VIII) are known (cf., for example, EP-A 154,115 and EP-A 201,852).

Formula (VI)) provides a general definition of the sulphenyl halides furthermore required as starting substances for carrying out process (d) according to the invention. In this formula (IV)), R² preferably represents those radicals which have already been mentioned in connection with the description of the substances of the formula (I) according to the invention as being preferred for this substituent.

Hal² preferably represents chlorine or bromine.

The sulphenyl halides of the formula (VI) are generally known compounds of organic chemistry.

Formula (Id) provides a general definition of the substituted 1-arylpyrazoles required as starting substances for carrying out process (e) according to the invention. In this formula (Id), R¹, R², R³, R⁴, A, X and Ar preferably represent those radicals which have already been mentioned in connection with the description of the substances of the formula (I) according to the invention as being preferred for these substituents.

The substituted 1-arylpyrazoles of the formula (Id) are compounds according to the invention and can be obtained with the aid of processes (a), (b), (c), (d) and (f) according to the invention.

Formula (Ig) provides a general definition of the substituted 1-arylpyrazoles required as starting substances for carrying out process (f) according to the invention. In this formula (Ig), R¹, R², R³, A, Ar and n preferably represent those radicals and indices which have already been mentioned in connection with the description of the substances of the formula (I) according to the invention as being preferred for these substituents and indices.

X¹ represents oxygen, sulphur or a radical of the formula

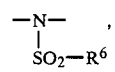

where R⁶ preferably represents those radicals which have already been mentioned in connection with the description of the substances of the formula (I) according to the invention as being preferred for this substituent.

The substituted 1-arylpyrazoles of the formula (Ig) are compounds according to the invention and can be obtained with the aid of processes (a), (b), (d) and (e) according to the invention.

Diluents which are suitable for carrying out process (a) according to the invention are inert organic solvents. These in particular include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If appropriate, process (a) according to the invention can also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-C₁₃/C₁₅-alkylammonium chloride, dibenzyl-dimethylammonium methylsulphate, dimethyl-C₁₂/C₁₄-alkylbenzylammonium chloride, tetrabutylammonium hydroxide, 15-crown-5, 18-crown-6, triethylbenzylammonium chloride or trimethylbenzylammonium chloride.

Reaction auxiliaries which are suitable for carrying out process (a) according to the invention are all inorganic and organic bases which can customarily be used. Hydrides, hydroxides, amides, alkoxides, carbonates or hydrogen carbonates of alkali metals, such as, for example, sodium hydride, sodium amide, sodium methoxide, sodium hydroxide, sodium carbonate or sodium hydrogen carbonate, and also tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU), are preferably used.

When carrying out process (a) according to the invention, the reaction temperatures can be varied within a substantial range. In general, the process is carried out between −20° C. and +150° C., preferably between 0° C. and +100° C.

For carrying out process (a) according to the invention, 1.0 to 20.0 moles, preferably 1.0 to 15.0 moles, of alkylating agent of the formula (III) and, if appropriate, 1.0 to 3.0 moles, preferably 1.0 to 2.0 moles, of reaction auxiliary and, if appropriate, 0.01 to 1.0 mole of phase transfer catalyst are generally employed per mole of 1-arylpyrazole of the formula (II). The reaction is carried out and the reaction products of the formula (I) are worked up and isolated in a generally customary fashion.

Diluents which are suitable for carrying out process (b) according to the invention are inorganic or organic polar solvents. Alcohols, such as, for example, methanol, ethanol or propanol, or their mixtures with water, are preferably used.

Catalysts which are preferably suitable for carrying out process (b) according to the invention are acids, in particular hydrochloric acid or sulphuric acid, or bases, in particular sodium hydroxide, sodium hydride or potassium t-butoxide.

When carrying out process (b) according to the invention, the reaction temperatures can be varied within a substantial range. In general, the process is carried out between +20° C. and +150° C., preferably between +50° C. an 120° C.

For carrying out process (b) according to the invention, 1.0 to 20.0 moles, preferably 1.0 to 10.0 moles, of catalyst acid or catalyst base are generally employed per mole of substituted 1-arylpyrazole of the formula (Ia), and the mixture is heated for several hours to the reaction temperature required. The reaction products of the formula (Ib) are worked up, isolated and purified by customary methods.

Diluents which are suitable for carrying out process (c) according to the invention are inert organic solvents. These preferably include aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If alcohols, amino compounds or thiols in liquid form are used as the reactants of the formula (IV), it is also possible to employ these in an appropriate excess, to act simultaneously as the diluent.

Process (c) according to the invention is preferably carried out in the presence of a suitable acylation catalyst. In principle, suitable acylation catalysts are all customary reaction auxiliaries which can be used for esterification and amidations. The following may be mentioned by way of example: acid halide formers, such as thionyl chloride, phosphorus trichloride, phosphorus pentachloride or phosphorus oxychloride, or activated ester components, such as N-hydroxy-succinimide, anhydride formers, such as 4-nitrophenyl chloroformate, or customary condensation agents, such as concentrated sulphuric acid, dicyclohexylcarbodiimide (DCC), triphenylphosphine as a mixture with carbon tetrachloride, N,N'-carbonyl-diimidazole or N-ethoxycarbonyl-2-ethoxy-dihydroquinoline (EEDQ).

Moreover, process (c) according to the invention can be carried out, if appropriate, in the presence of a suitable reaction auxiliary. Reaction auxiliaries which are suitable are all customary inorganic or organic bases. These include, for example, alkali metal hydroxides, such as sodium hydroxdide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU). A suitable excess of one of the amines used simultaneously as the reactant of the formula (IV) can also serve as reaction auxiliary, if appropriate.

When carrying out process (c) according to the invention, the reaction temperatures can be varied within a substantial range. In general, the process is carried out at temperatures between −20° C. and +150° C., preferably at temperatures between 0° C. and +100° C.

For carrying out process (c) according to the invention, 1.0 to 20.0 moles, preferably 1.0 to 10.0 moles, of alcohol, amino compound or thiol of the formula (IV), 1.0 to 5.0 moles, preferably 1.0 to 2.0 moles, of acylation catalyst and, if appropriate, 1.0 to 2.0 moles of reaction auxiliary are generally employed per mole of substituted 1-arylpyrazole of the formula (Ib).

In most cases, it is advantageous to first prepare an activated complex (acid halide, activated ester, mixed acid anhydride etc.) from the substituted 1-arylpyrazole of the formula (Ib) and the acylation catalyst, and, if appropriate, this activated complex can be isolated and reacted with the alcohol, amine or thiol of the formula (IV) either in a separate reaction step or in a one-pot process. Depending on the nature of the acylation catalyst used, addition of the reaction auxiliary can be useful either in step 1 for the formation of the activated complex or in step 2 for the reaction of the latter. The reaction is carried out and the reaction products of the formula (Ic) are worked up and isolated by generally customary processes.

Diluents which are suitable for carrying out process (d) according to the invention are inert organic solvents. These in particular include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or acids, such as, for example, acetic acid.

If appropriate, process (d) according to the invention can be carried out in the presence of a reaction auxiliary. Reaction auxiliaries which are suitable are all customary inorganic or organic bases. These include, for example, alkali metal hydroxides, such as sodium hydroxdide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures between −20° C. and +120° C., preferably at temperatures between 0° C. and +50° C.

For carrying out process (d) according to the invention, 1.0 to 2.5 moles, preferably 1.0 to 1.5 moles, of sulphenyl halide of the formula (VI) and, if appropriate, 1.0 to 2.5 moles, preferably 1.0 to 1.5 moles, of reaction auxiliary are generally employed per mole of 1-arylpyrazole which is unsubstituted in the 4-position, of the formula (V). The reaction is carried out and the reaction products of the formula (Id) are worked up and isolated by generally customary methods.

Oxidants which are suitable for carrying out process (e) according to the invention are all customary oxidants which can be used for the oxidation of sulphur. The following oxidants are particularly suitable: hydrogen peroxide, organic peracids, such as, for example, peracetic acid, m-chloroperbenzoic acid or p-nitroperbenzoic acid, or atmospheric oxygen.

Diluents which are suitable for carrying out process (e) according to the invention are also inert organic solvents. The following are preferably used: hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide.

If appropriate, process (e) according to the invention can be carried out in the presence of an acidbinding agent. Suitable acid-binding agents are all organic and inorganic acid-binding agents which can customarily be used. The following are preferably used: hydroxides, acetates or carbonates of alkaline earth metals or alkali metals, such as, for example, calcium hydroxide, sodium hydroxide, sodium acetate or sodium carbonate.

If appropriate, process (e) according to the invention can be carried out in the presence of a suitable catalyst. Catalysts which are suitable are all metal salt catalysts which are customarily used for sulphur oxidations of this type. Ammonium molybdate may be mentioned in this connection by way of example.

When carrying out process (e) according to the invention, the reaction temperatures can be varied within a substantial range. In general, the process is carried out at temperatures between −20° C. and +70° C., preferably at temperatures between 0° C. and +50° C.

For carrying out process (f) according to the invention, 0.8 to 1.2 moles, preferably equimolar amounts, of oxidant are generally employed per mole of substituted 1-arylpyrazole of the formula (Id) if it is desired to interrupt the oxidation of sulphur at the sulphoxide level. For oxidation to give the sulphone, 1.8 to 3.0 moles, preferably twice the molar amounts, of oxidant are generally employed per mole of substituted 1-arylpyrazole of the formula (Id). The reaction is carried out and the end products of the formula (Ie) are worked up and isolated by customary processes.

Process (f) according to the invention is carried out in the presence of an inorganic or organic base. Bases which are used are hydroxides, oxides or carbonates of alkali metals or alkaline earth metals or suitably substituted amines, depending on the nature of the desired counterion $M^\oplus$ in the compounds of the formula (If).

Diluents which are suitable for carrying out process (f) according to the invention are organic or aqueous solvents or organic-aqueous solvent mixtures. Alcohols, such as methanol, ethanol or propanol, or their mixtures with water, as well as pure water, are preferably used as diluents.

When carrying out process (f) according to the invention, the reaction temperatures can be varied within a substantial range. In general, the process is carried out at temperatures between −20° C. and +120° C., preferably at temperatures between 0° C. and 80° C.

For carrying out process (f) according to the invention, 1.0 to 20.0 moles, preferably 1.0 to 10.0 moles, of base are generally employed per mole of substituted 1-arylpyrazole of the formula (Ig). The calcium, barium, magnesium, manganese, copper, nickel, tin, iron and cobalt salts are also obtained from the sodium salts by treating them with a corresponding inorganic metal salt, for example calcium chloride, barium chloride, copper sulphate, nickel chloride or cobalt nitrate. The salts of the formula (If) are worked up and isolated by customary methods.

The active compounds of the general formula (I) are suitable for combating animal pests, in particular insects, arachnida and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*. From the order of the Dermaptera, for example, *Forficula auricularia*. From the order of the Isoptera, for example, *Reticulitermes spp*. From the order of the Anoplura, for example, *Phylloxera vastatrix, Pemphigus spp., Pediculus humanus corporis, Haematopinus spp.* and *Linognathus spp*. From the order of the Malophaga, for example, *Trichodectes spp.* and *Damalinea spp*. From the order of the Thysanoptera, for example, *Hercinothrips femoralis* and *Thrips tabaci*. From the order of the Heteroptera, for example, *Eurygaster spp., Dysdercus intermedius, Piesma quadrate, Cimex lectularius, Rhodnius prolixus* and Triatoma spp. From the order of the Homoptera, for example, *Aleurodes brassicae, Bemisia tabaci, Trialeurodes vaporariorum, Aphis gossyoii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp*. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia* ni, *Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma ssp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.* From the order of the Hymenoptera, for example, *Diprion spp., Hoplocampa spp., Lasius spp., Monomorium pharaonis* and *Vespa ssp.* From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.* From the order of the Siphonaptera, for example, *Xenopsylla cheopis* and *Ceratophyllus spp.* From the order of the Arachnida, for example, *Scorpio maurus* and *Latrodectus mactans.*

From the order of the Acarina, for example, *Acarus siro, Argas spp., Ornithodoros spp., Dermanyssus gallinae, Eriophves ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and endoparasitically living worms.

They are active against normally sensitive and resistant species and strains, as well as against all parasitic and non-parasitic stages of development of the ecto- and endoparasites.

The active compounds according to the invention have a strong insecticidal action. They can be employed particularly successfully against insects which are harmful to plants, such as, for example, against the caterpillar of the owlet moth (*Spodoptera frugiperda*) and the larvae of the mustard beetle (*Phaedon cochleariae*) or against the green peach aphid (*Mycus persicae*), and for the control of soil insects, such as, for example, against the grubs of the onion fly (*Phorbia anticua*) or of *Diabrotica balteata* larvae in the soil. In this connection, the active compounds according to the invention also show systemic properties and are therefore particularly suitable as seed treatment agents.

The active compounds according to the invention can additionally be employed with particularly good success for combating pests which live as parasites on warm-blooded animals, such as, for example, against cattle ticks (*Boophilus microplus*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks, such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as moulded articles (collar, ear tag) is also possible.

The biological effectiveness of the compounds according to the invention will be explained with reference to the examples below.

PREPARATION EXAMPLES

Example 1

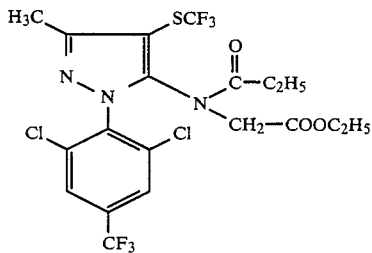

(Process a)

3.4 ml (0.03 mol) of ethyl bromoacetate are added dropwise with stirring at room temperature to a mixture of 9.3 g (0.02 mol) of 1-(2,6-dichloro-4-trifluoromethylphenyl)-3-methyl-4-trifluoromethylthio-5-propionamidopyrazole (cf., for example, European Patent No. 201,852) and 0.87 g (0.03 mol) of sodium hydride (80% pure in paraffin) in 90 ml of absolute tetrahydrofuran; when the addition is complete, the mixture is stirred for 3 more hours at room temperature, 100 ml of saturated aqueous ammonium chloride solution are then added, the mixture is extracted several times using dichloromethane, the combined organic extracts are washed with saturated aqueous sodium chloride solution and dried over sodium sulphate, and the solvent is removed in vacuo.

This gives 11.1 g (100% of theory) of ethyl N-propionyl-N-[1-(2,6-dichloro-4-trifluoromethylphenyl)-3-methyl-4-trifluoromethylthio-5-pyrazolyl]-glycinate of melting point 73° C. to 74° C.

Example 2

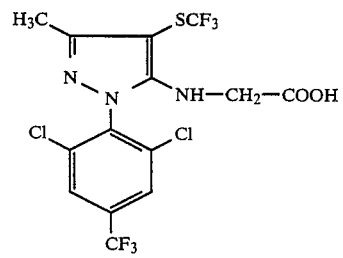

(Process b)

6 g (0.011 mol) of ethyl N-propionyl-N-[1-(2,6-dichloro-4-trifluoromethylphenyl)-3-methyl-4-trifluoromethylthio-5-pyrazolyl]-glycinate are stirred for about 8 hours at 50° C. in 25 ml of 80% strength sulphuric acid. The reaction mixture is then transferred into 200 ml of ice-water, the precipitated product is filtered off and dissolved in 2-normal sodium hydroxide solution, the solution is washed with dichloromethane, precipitation is then induced again by acidifying the solution with icecooling, and the product is filtered off with suction, washed with water and dried.

This gives 4.3 g (84% of theory) of N-[1-(2,6-dichloro-4-trifluoromethylphenyl)-3-methyl-4-trifluoromethylthio-5-pyrazolyl]-glycine of melting point 168°-170° C.

Example 3

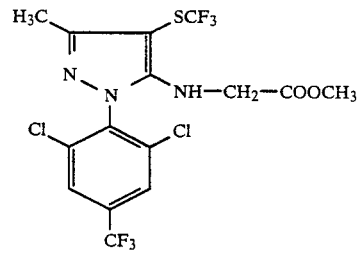

(Process c)

A solution of 3 g (0.0062 mol) of N-[1-(2,6-dichloro-4-trifluoromethylphenyl)-3-methyl-4-trifluoromethylthio-5-pyrazolyl]-glycine and 0.9 ml of concentrated sulphuric acid in 30 ml of absolute methanol is stirred for 4 hours at 20° C. and then concentrated in vacuo, the residue is taken up in ether, and the solution is washed with saturated aqueous sodium hydrogen carbonate solution, dried over sodium sulphate and concentrated in vacuo.

This gives 2.3 g (77% of theory) of methyl N-[1-(2,6-dichloro-4-trifluoromethylphenyl)-3-methyl-4-trifluoromethylthio-5-pyrazolyl]-glycinate as an oil.

$^1$H—NMR (CDCl$_3$/tetramethylsilane): δ=7.77 (s, 2H, aryl) ppm.

Example 4

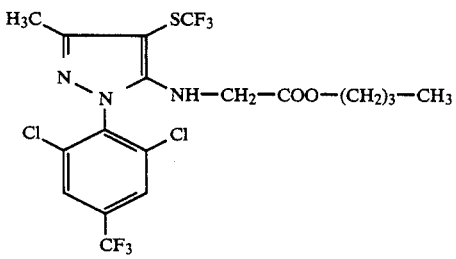

(process c)

A mixture of 4.7 g (0.01 mol) of N-[1-(2,6-dichloro-4-trifluoromethylphenyl)-3-methyl-4-trifluoromethylthio-5-pyrazolyl]-glycine, 2.1 g (0.01 mol) of phosphorus pentachloride and 100 ml of absolute ether is refluxed for 15 minutes and then concentrated in vacuo, the residue is taken up in 50 ml of n-butanol, and the solution is stirred for 16 hours at room temperature. For working up, the mixture is concentrated in vacuo, the residue is taken up in dichloromethane, and the solution is washed with water, dried over sodium sulphate and freed from the solvent in vacuo.

This gives 3.5 g (67% of theory) of N-[1-(2,6-dichloro-4-trifluoromethylphenyl)-3-methyl-4-trifluoromethylthio-5-pyrazolyl]-glycinate as an oil.

$^1$H—NMR (CDCl$_3$/tetramethylsilane): δ=7.75 ppm (s, 2H, aryl).

Example 5

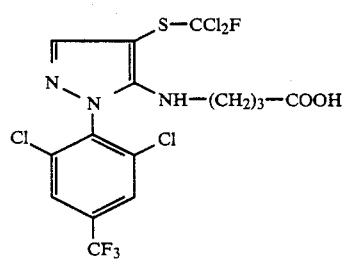

(Process d)

3.3 ml (0.0315 mol) of dichlorofluoromethanesulphenyl chloride are added dropwise with stirring at 15° C. to 10 g (0.0262 mol) of N-[1-(2,6-dichloro-4-trifluoromethylphenyl)-5-pyrazolyl]-4-aminobutyric acid in 40 ml of glacial acetic acid, the reaction mixture is subsequently stirred for 5 hours at room temperature and then transferred into ice-water, and the product which has precipitated is filtered off with suction, washed with water and dried in vacuo at 50° C.

This gives 12.0 g (89% of theory) of N-[1-(2,6-dichloro-4-trifluoromethylphenyl)-4-dichlorofluoromethanesulphenyl-5-pyrazolyl]-4-aminobutyric acid of melting point 99° C. to 101° C.

PREPARATION OF THE STARTING COMPOUND

Example V-1

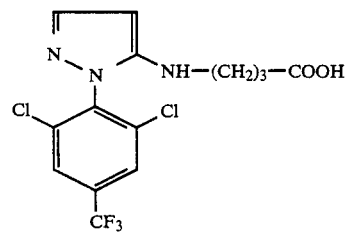

61.5 g (0.169 mol) of 1-[1-(2,6-dichloro-4-trifluoromethylphenyl)-5-pyrazolyl]-pyrrolidin-2-one are refluxed with stirring for 24 hours in 250 ml of 48 per cent strength hydrobromic acid. For working up, the in water, the mixture is neutralized using 4 per cent strength aqueous sodium hydroxide solution, the solid which has precipitated is washed and dried and taken up in n-hexane, the mixture is stirred, and the precipitate is again filtered with suction and dried at 50° C. in vacuo.

This gives 39.4 g (61% of theory) of N-[1-(2,6-dichloro-4-trifluoromethylphenyl)-5-pyrazolyl]-4-aminobutyric acid of melting point 160°–162° C.

Example IX-1

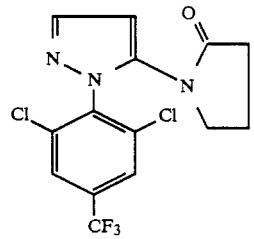

30 ml of concentrated ammonia water are added to 67.7 g (0.169 mol) of 5-(4-chlorobutanoyl)-amino-1-(2,6-dichloro-4-trifluoromethylphenyl)-pyrazole (cf., for example, European Patent No. 154,115) in 120 ml of ethanol, the mixture is stirred for 24 hours at room temperature and concentrated in vacuo, and the resulting crude product is directly reacted further to Example V-1.

This gives 61.5 g (98% of theory) of 1-[1-(2,6-dichloro-4-trifluoromethylphenyl)-5-pyrazolyl]-pyrrolidin-2-one of melting point 130°–131° C.

Example VIII-1

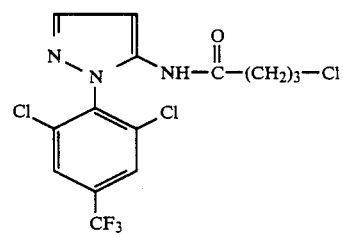

In a first step, 15 ml (0.186 mol) of anhydrous pyridine are added to 50 g (0.169 mol) of 5-amino-1-(2,6-dichloro-4-trifluoromethylphenyl)-pyrazole (cf. European Patent No. 154,115) in 250 ml of acetonitrile, and 20.3 ml (0.178 mol) of 4-chlorobutanoyl chloride are then added dropwise with stirring at room temperature, during which process the temperature of the reaction mixture rises to 30° C. When the addition is complete, the reaction mixture is stirred for one more hour at room temperature and then transferred, with stirring, into 1,000 ml of water, and the product which has precipitated is filtered off with suction and dried in vacuo at 50° C.

This gives 67.7 g (100% of theory) of 5-(4-chlorobutanoylamino)-1-(2,6-dichloro-4-trifluoromethylphenyl)-pyrazole of melting point 103° to 104° C.

The following substituted 1-arylpyrazoles of the general formula (I) are obtained in a corresponding manner and following the general preparation instructions:

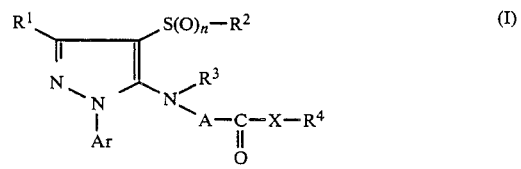

| Example No. | $R^1$ | $R^2$ | n | $R^3$ | $-A-\underset{\underset{O}{\|}}{C}-X-R^4$ | Ar | physical properties |
|---|---|---|---|---|---|---|---|
| 6 | $CH_3$ | $CF_3$ | 0 | H | $-CH_2-COOC_2H_5$ | 2,6-Cl$_2$-4-CF$_3$-C$_6$H$_2$ | $^1$H-NMR*: 7.77 |
| 7 | $CH_3$ | $CF_3$ | 0 | H | $-CH_2-COO-(CH_2)_2-CH_3$ | 2,6-Cl$_2$-4-CF$_3$-C$_6$H$_2$ | $^1$H-NMR*: 7.78 |
| 8 | $CH_3$ | $CF_3$ | 0 | H | $-CH_2-COO-CH(CH_3)_2$ | 2,6-Cl$_2$-4-CF$_3$-C$_6$H$_2$ | $^1$H-NMR*: 7.78 |
| 9 | $CH_3$ | $CF_3$ | 0 | H | $-CH_2-COO-CH_2-C_6H_5$ | 2,6-Cl$_2$-4-CF$_3$-C$_6$H$_2$ | $^1$H-NMR*: 7.72 |
| 10 | $CH_3$ | $CF_3$ | 0 | H | $-CH_2-CO-N(CH_3)_2$ | 2,6-Cl$_2$-4-CF$_3$-C$_6$H$_2$ | Fp 109° C. |
| 11 | H | $CF_3$ | 0 | $-\underset{\underset{O}{\|}}{C}-CH_3$ | $-COOC_2H_5$ | 2,6-Cl$_2$-4-CF$_3$-C$_6$H$_2$ | Fp 70–73° C. |

-continued
| Example No. | R¹ | R² | n | R³ | $-A-\overset{O}{\overset{\|}{C}}-X-R^4$ | Ar | physical properties |
|---|---|---|---|---|---|---|---|
| 12 | H | CF₃ | 0 | H | —COOH | 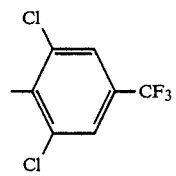 | Fp 97° C. (Zers.) |
| 13 | H | CF₃ | 0 | H | —COOH | 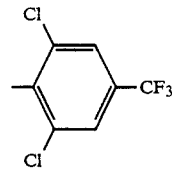 | Fp 101–103° |
| 14 | H | CF₃ | 1 | H | —(CH₂)₃—COOH | 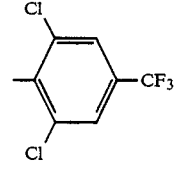 | ¹H-NMR*: 7.90 |
| 15 | H | CF₃ | 2 | H | —(CH₂)₃—COOH | 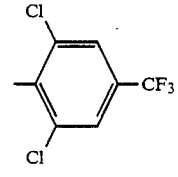 | Fp: 98–101° |
| 16 | H | —CCl₂F | 1 | H | —(CH₂)₃—COOH | 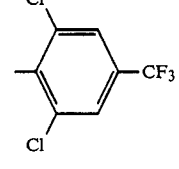 | ¹H-NMR* 7.85 |
| 17 | H | —CCl₂F | 2 | H | —(CH₂)₃—COOH | 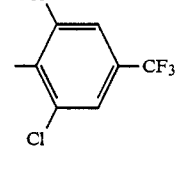 | Fp: 108–116° |
| 18 | H | CF₃ | 0 | H | —(CH₂)₃—COOC₂H₅ | 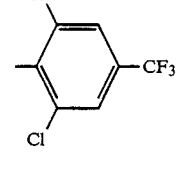 | ¹H-NMR* 7.67 |
| 19 | H | —CCl₂F | 0 | H | —(CH₂)₃—COOC₂H₅ | 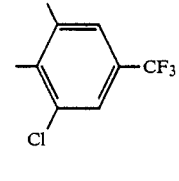 | ¹H-NMR* 7.72 |

-continued

| Example No. | $R^1$ | $R^2$ | n | $R^3$ | $-A-\overset{\overset{O}{\|}}{C}-X-R^4$ | Ar | physical properties |
|---|---|---|---|---|---|---|---|
| 20 | H | $-CCl_2F$ | 0 | $-\overset{\overset{O}{\|}}{C}-CH_3$ | $-CH_2-COOC_2H_5$ | 2,6-Cl$_2$-4-CF$_3$-C$_6$H$_2$- | Fp: 104–107° |
| 21 | H | $-CCl_2F$ | 1 | H | $-(CH_2)_3-COOC_2H_5$ | 2,6-Cl$_2$-4-CF$_3$-C$_6$H$_2$- | $^1$H-NMR* 7.91 |
| 22 | H | $-CCl_2F$ | 2 | H | $-(CH_2)_3-COOC_2H_5$ | 2,6-Cl$_2$-4-CF$_3$-C$_6$H$_2$- | $^1$H-NMR* 7.89 |
| 23 | H | $-CCl_2F$ | 0 | H | $-CH_2-COOH$ | 2,6-Cl$_2$-4-CF$_3$-C$_6$H$_2$- | Fp: 156–159° |
| 24 | H | $CF_3$ | 1 | H | $-(CH_2)_3-COOC_2H_5$ | 2,6-Cl$_2$-4-CF$_3$-C$_6$H$_2$- | $^1$H-NMR* 7.95 |
| 25 | H | $CF_3$ | 2 | H | $-(CH_2)_3-COOC_2H_5$ | 2,6-Cl$_2$-4-CF$_3$-C$_6$H$_2$- | $^1$H-NMR* 7.87 |
| 26 | H | $CF_3$ | 0 | H | $-CH_2-COOC_2H_5$ | 2,6-Cl$_2$-4-CF$_3$-C$_6$H$_2$- | Fp: 64–70° C. |
| 27 | H | $-CCl_2F$ | 0 | H | $-CH_2-COOC_2H_5$ | 2,6-Cl$_2$-4-CF$_3$-C$_6$H$_2$- | |

*The $^1$H-NMR spectra were recorded in deuterochloroform (CDCl$_3$) with tetramethylsilane (T) the internal standard. The chemical shift of the phenyl protons in the Ar substituent indicated as δ value in ppm.

USE EXAMPLES

In the Use Examples which follow, the compounds listed below are employed as comparison substances:

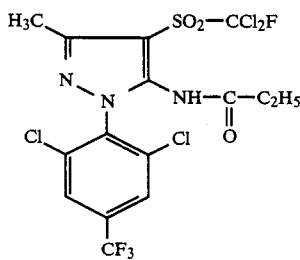

1-(2,6-dichloro-4-trifluoromethylphenyl)-3-methyl-4-dichlorofluoromethylsulphonyl-5-propionamidopyrazole

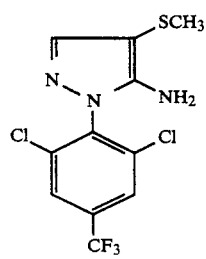

5-amino-1-(2,6-dichloro-4-trifluoromethylphenyl)-4-methylthio-pyrazole

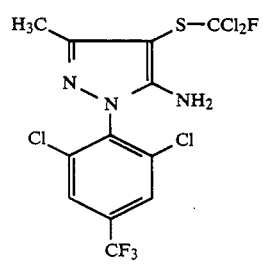

5-amino-1-(2,6-dichloro-4-trifluoromethylphenyl)-3-methyl-4-dichloromethylthio-pyrazole

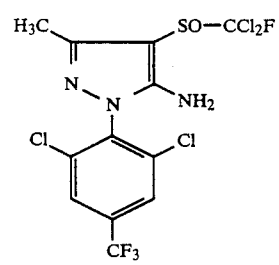

5-amino-1-(2,6-dichloro-4-trifluoromethylphenyl)-3-methyl-4-dichlorofluoromethylsulphinyl-pyrazole

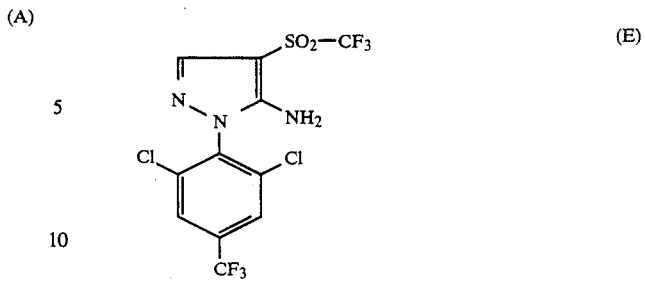

5-amino-1-(2,6-dichloro-4-trifluoromethylphenyl)-4-trifluoromethylsulphonyl-pyrazole (all known from European Patent No. 201,852)

EXAMPLE A

Myzus test (long-term action after watering)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which are heavily infested with peach aphids (Myzus persicae) are treated by being dipped into a preparation of active compound of the desired concentration.

After the specified periods of time, the destruction in % is determined. 100% means that all the aphids have been killed; 0% means that none of the aphids have been killed.

In this test, a superior activity compared with the prior art is shown, for example, by the following compounds of the Preparation Examples: 3, 13, 23 and 26.

EXAMPLE B

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the specified periods of time, the destruction in % is determined. 100% means that all the beetle larvae have been killed; 0% means that none of the beetle larvae have been killed.

In this test, a superior activity compared with the prior art is shown, for example, by the following compounds of the Preparation Examples: 3, 26 and 27.

EXAMPLE C

Spodoptera test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the specified periods of time, the destruction in % is determined. 100% means that all the caterpillars have been killed; 0% means that none of the caterpillars have been killed.

In this test, a superior activity compared with the prior art is shown, for example, by the following compounds of the Preparation Examples: 16, 17, 23, 26 and 27.

EXAMPLE D

Critical concentration test/soil insects

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/1), being decisive. The soil is transferred into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, a superior activity compared with the prior art is shown, for example, by the following compounds of the Preparation Examples: 2, 3, 4, 6, 7, 8, 9, 10, 14 and 17.

EXAMPLE E

Critical concentration test/soil insects

Test insect: *Diabrotica balteata* larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (=mg/1), being decisive. The soil is transferred into pots and the pots are left to stand at 20° C.

Immediately after preparation, 6 pre-germinated maize seeds are placed in each pot. After 2 days the corresponding test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, a superior activity compared with the prior art is shown, for example, by the following compounds of the Preparation Examples: 2 and 3.

EXAMPLE F

Critical concentration test/root-systemic action

Test insect: *Phaedon cochleariae*—larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/1), being decisive. The treated soil is transferred into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, a superior activity compared with the prior art is shown, for example, by the following compounds of the Preparation Examples: 1, 2, 3, 4, 6, 7, 8, 9, 10, 12, 14 and 16.

EXAMPLE G

Critical concentration test/root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/1), being decisive. The treated soil is transferred into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, a superior activity compared with the prior art is shown, for example, by the following compounds of the Preparation Examples: 3 us 12.

EXAMPLE H

Seed treatment test/soil insects

Test insect: *Phorbia antiqua* grubs in the soil
Test plant: *Allium cepa*
Solvent: 1 part by weight of acetone
Carrier: kaolin To produce a suitable preparation of active compound, the active compound is dissolved in acetone and 1 part by weight of active compound/acetone is mixed with 5 parts by weight of kaolin. The onion seeds are treated with this active compound preparation at the application rates required. They are sown in 0.5 liter pots containing standardized soils at a greenhouse temperature of 20° C.

After emergence of the onions, they are artificially infected with onion fly eggs.

Evaluation is carried out after 14 days. The degree of action is 100% if all the onion plants remain standing, and 0% if all the test plants have been destroyed (as in the untreated control).

In this test, a superior action compared with the prior art is shown, for example, by the following compounds of the Preparation Examples: 2, 3 and 12.

EXAMPLE I

Seed treatment test/root-systemic action

Test insect: *Phaedon cochleariae* beetles
Test plant: *Brassica oleracea*
Solvent: 1 part by weight of acetone
Carrier: kaolin To produce a suitable preparation of active compound, the active compound is dissolved in acetone, and 1 part by weight of active compound/acetone is mixed with 5 parts by weight of kaolin. The cabbage seeds are treated with this active compound preparation at the application rates required. The cabbage is sown in 0.5 liter pots containing standardized soils at a room temperature of 20° C.

The active compound can thus be taken up from the soil by the plant roots and transported into the leaves.

For detection of the root-systemic effect, exclusively the leaves are infested with the abovementioned test animals after 14 days. After a further 3 days, the evaluation is carried out by counting or estimating the dead animals. The root-systemic action of the active compound is derived from the destruction killed and 0% if just as many test insects are still alive as in the untreated control.

In this test, a superior action compared with the prior art is shown, for example, by the following compounds of the Preparation Examples: 2, 3 and 12.

EXAMPLE K

Tick test (*Boophilus microplus*)/Inhibition of egg deposition

Solvent: 35 parts by weight of ethylene glycol monomethyl ether
35 parts by weight of nonylphenol polyglycol ether To produce a suitable formulation, three parts by weight of active compound are mixed weight of the abovementioned solvent/emulsifier mixture, and the emulsion concentrate thus obtained is diluted with water to the specific desired concentration.

Adult female ticks which have sucked themselves full of the species Boophilus microplus (sensitive and resistant, respectively) are immersed for one minute in this active compound preparation After 10 female specimens of each of the different tick species have been immersed, they are transferred into Petri dishes in which a filterpaper disc of appropriate size has been placed on the bottom.

After 10 days, the effectiveness of the active compound preparation is determined by comparing the inhibition of egg deposition with untreated control ticks. The action is expressed as a percentage, 100% denoting that no eggs were deposited any longer and 0% denoting that the ticks deposited normal amounts of eggs.

In this test, a superior action compared with the prior art is shown, for example, by the following compounds of Preparation Examples 1 and 20.

What is claimed is:

1. A substituted 1-arylpyrazole of the formula (I)

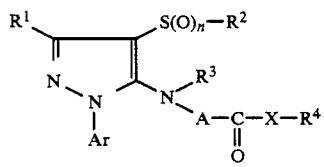

in which
R¹ represents hydrogen or alkyl,
R² represents alkyl or halogenoalkyl,
R³ represents hydrogen or alkanoyl,
R⁴ represents hydrogen, alkyl, hydroxyalkyl, alkoxyalkyl, alkylthioalkyl, halogenoalkyl, alkenyl, halogenoalkenyl or alkinyl, or represents in each case optionally substituted cycloalkyl, aralkyl or aryl, or, when X represents oxygen or sulphur, also represents a cation,
A represents a double-linked alkylene radical,
X represents oxygen, sulphur or a radical

Ar represents optionally substituted phenyl or optionally substituted pyridyl and
n represents a number 0, 1 or 2, where
R⁵ represents hydrogen, alkyl, hydroxyalkyl, alkoxyalkyl, alkylthioalkyl, halogenoalkyl, alkenyl, halogenoalkenyl or alkinyl, or represents optionally substituted cycloalkyl, aralkyl or aryl.

2. A substituted 1-arylpyrazole according to claim 1, in which

R¹ represents hydrogen or alkyl having 1 to 6 carbon atoms,

R² represents alkyl having 1 to 6 carbon atoms or halogenoalkyl having 1 to 4 carbon atoms and 1 to 9 identical or different halogen atoms, R³ represents hydrogen or alkanoyl having 1 to 5 carbon atoms, R⁴ represents hydrogen, alkyl or hydroxyalkyl, each of which has 1 to 12 carbon atoms, alkoxyalkyl or alkylthioalkyl, each of which has 2 to 12 carbon atoms, alkenyl or alkinyl, each of which has 2 to 12 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, cycloalkyl which has 3 to 7 carbon atoms and which is optionally substituted by identical or different alkyl substituents which have 1 to 4 carbon atoms, or represents phenyl, benzyl or phenylethyl, each of which is optionally substituted in the phenyl moiety by identical or different substituents, suitable phenyl substituents in each case being: halogen, cyano, nitro, in each case alkyl, alkoxy or alkylthio, each of which has 1 to 4 carbon atoms, halogenoalkyl, halogenoalkoxy or halogenoalkylthio, each of which has 1 to 4 carbon atoms and 1 to 9 identical or different halogen atoms, alkoxycarbonyl or alkoximinoalkyl, each of which has 1 to 4 carbon atoms in the individual alkyl moieties, and phenyl which is optionally substituted by halogen and/or alkyl having 1 to 4 carbon atoms; and, furthermore, when X represents oxygen or sulphur, R⁴ can represent one equivalent of an alkali metal, alkaline earth metal, copper, zinc, manganese, tin, iron-cobalt or nickel cation or an ammonium, phosphonium or sulphonium cation, each of which is optionally substituted by identical or different substituents, suitable substituents being: alkyl having 1 to 18 carbon atoms, phenyl or benzyl, A represents a double-linked alkylene radical having 1 to 12 carbon atoms, X represents oxygen, sulphur or a radical

Ar represents phenyl, 2-pyridyl, 3-pyridyl or 4-pyridyl, each of which is optionally substituted by identical or different substituents, suitable substituents in each case being: cyano, nitro, halogen, alkyl, alkoxy or alkoxycarbonyl, each of which has 1 to 4 carbon atoms, halogenoalkyl or halogenoalkoxy, each of which has 1 to 4 carbon atoms and 1 to 9 identical or different halogen atoms, or a radical —S(O)$_p$—R⁶ and n represents a number 0, 1 or 2, where R⁵ represents hydrogen, alkyl or hydroxyalkyl, each of which has 1 to 12 carbon atoms, alkoxyalkyl or alkylthioalkyl, each of which has 2 to 12 carbon atoms, alkenyl or alkinyl, each of which has 2 to 12 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, or cycloalkyl which has 3 to 7 carbon atoms and which is optionally substituted by identical or different alkyl substituents which have 1 to 4 carbon atoms, or represents phenyl, benzyl or phenylethyl, each of which is optionally substituted in the phenyl moiety by identical or different substituents, suitable phenyl substituents in each case being: halogen, cyano, nitro, alkyl, alkoxy or alkylthio, each of which has 1 to 4 carbon atoms, halogenoalkyl, halogenoalkoxy or halogenoalkylthio, each of which has 1 to 4 carbon atoms and 1 to 9 identical or different halogen atoms, alkoxycarbonyl or alkoximinoalkyl, each of which has 1 to 4 carbon atoms in the individual alkyl moieties, and also phenyl which is optionally substituted halogen and/or alkyl having 1 to 4 carbon atoms;

R⁶ represents amino, alkyl, alkylamino, dialkylamino or halogenoalkyl, in each case having 1 to 4 carbon atoms in the individual alkyl moieties and, in the case of the halogenoalkyl, 1 to 9 identical or different halogen atoms, and p represents a number 0, 1 or 2.

3. A substituted 1-arylpyrazole according to claim 1, in which

R¹ represents hydrogen, methyl, ethyl, n- or i-propyl, n-, i-, s- or t-butyl,

R² represents methyl, ethyl, n- or i-propyl, n-, i-, s- or t-butyl, chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl or bromopropyl, R³ represents hydrogen, acetyl, propionyl or butyryl, R⁴ represents hydrogen, or methyl, ethyl, n- or ipropyl, n-, i-, s- or t-butyl or n- or i-pentyl, each of which is optionally substituted fluorine, chlorine, hydroxyl, methoxy, ethoxy, methylthio or ethylthio, or R⁴ represents allyl, propenyl or butenyl, each of which is optionally substituted by identical or different substituents selected from the group consisting of fluorine and chlorine, or R⁴ represents propargyl, propinyl, butinyl or pentinyl, or cyclopropyl, cyclopentyl or cyclohexyl, or benzyl or phenyl, each of which is optionally substituted by identical or different substituents selected from the group consisting of fluorine, chlorine, bromine, cyano, nitro, methyl, ethyl, methoxy, ethoxy, methylthio or trifluoromethyl, and, when X represents oxygen or sulphur, R⁴ can represent one equivalent of a sodium, potassium, magnesium, calcium, barium, copper, zinc, manganese, tin, iron, cobalt or nickel cation, each of which is optionally substituted by identical or different substituents selected from the group consisting of methyl, ethyl, n- or i-propyl, n-, i-, s- or t-butyl, benzyl or phenyl, A represents a double-linked alkylene radical having 1 to 6 carbon atoms, X represents oxygen, sulphur or a radical

Ar represents phenyl which is optionally substituted by identical or different substituents, or 2-pyridyl which is optionally substituted by identical or different substituents, suitable substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $-S(O)_p-R^6$ and n represents a number 0, 1 or 2, where $R^5$ represents hydrogen, or methyl, ethyl, n- or i-propyl, n-, i-, s- or t-butyl or n- or i-pentyl, each of which is optionally substituted by identical or different substituents selected from the group consisting of fluorine, chlorine, hydroxyl, methoxy, ethoxy, methylthio or ethylthio, or $R^5$ represents allyl, propenyl or butenyl, each of which is optionally substituted by identical or different substituents selected from the group consisting of fluorine and chlorine, or $R^5$ represents propargyl, propinyl, butinyl or pentinyl, or cyclopropyl, cyclopentyl or cyclohexyl, or represents benzyl or phenyl, each of which is optionally substituted by identical or different substituents selected from the group consisting of fluorine, chlorine, bromine, cyano, nitro, methyl, ethyl, methoxy, ethoxy, methylthio and trifluoromethyl, $R^6$ represents amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, and p represents a number 0, 1 or 2.

4. A substituted 1-arylpyrazole according to claim 1, in which $R^1$ represents hydrogen or methyl, $R^2$ represents trifluoromethyl, dichlorofluoromethyl or chlorodifluoromethyl, $R^3$ represents hydrogen, acetyl or propionyl, $R^4$ represents hydrogen, methyl, ethyl, n- or i-propyl, n-, i-, s- or t-butyl or benzyl, A represents a radical of the formula $-CH_2-$; $-CH_2-CH_2-$; $-CH_2-CH_2-CH_2-$ or

X represents oxygen or a radical

Ar represents phenyl which is optionally substituted by identical or different substituents selected from the group consisting of fluorine, chlorine, bromine, trifluoromethyl and trifluoromethoxy and n represents a number 0, 1 or 2, where $R^5$ represents methyl, ethyl, n- or i-propyl, n-, i-, s- or t-butyl or a radical $-SO_2O-R^6$ and $R^6$ represents methyl, trifluoromethyl, phenyl or p-tolyl.

5. A pesticidal composition useful for combating insects, arachnida and nematodes comprising at least one as substituted 1-arylpyrazole according to claim 1 and a suitable extender or carrier.

6. A method of combating insects, arachnida or nematodes comprising applying an effective amount of at least one substituted 1-arylpyrazole according to claim 1 to said insects, arachnida or nematodes or an environment thereof.

* * * * *

UNITED STATES PATENT AND TRADEMARK OFFICE
CERTIFICATE OF CORRECTION

PATENT NO. : 4,971,989

DATED : November 20, 1990

INVENTOR(S) : Jensen-Korte et al.

It is certified that error appears in the above-identified patent and that said Letters Patent is hereby corrected as shown below:

Col. 42, line 28  Delete " $SO_2O$ " and substitute -- $SO_2$ --

Signed and Sealed this

Thirteenth Day of October, 1992

Attest:

DOUGLAS B. COMER

Attesting Officer      Acting Commissioner of Patents and Trademarks